United States Patent [19]

Nakanishi et al.

[11] Patent Number: 4,694,080

[45] Date of Patent: Sep. 15, 1987

[54] 2H-1,2-BENZOTHIAZINE DERIVATIVES

[75] Inventors: Susumu Nakanishi; Isao Nagakura, both of Aichi, Japan

[73] Assignee: Pfizer Inc., New York, N.Y.

[21] Appl. No.: 841,509

[22] Filed: Mar. 19, 1986

[30] Foreign Application Priority Data

Apr. 16, 1985 [JP] Japan .................................. 60-80666

[51] Int. Cl.[4] .................... C07D 417/04; A61K 31/38
[52] U.S. Cl. ...................................................... 544/49
[58] Field of Search ........................... 544/49; 514/225

[56] References Cited

U.S. PATENT DOCUMENTS 3,303,189  2/1967  Loeu ...................................... 544/49
3,957,772  5/1976  Fabian et al. .......................... 544/49

OTHER PUBLICATIONS

E. P. 115-748-A (Abstract) 8/15/84.
Shen et al., "*The Development of Antiasthmatic Drugs*", Butterworth Publishers, Kent, England, pp. 316–317 and 331–335.

*Primary Examiner*—Henry R. Jiles
*Assistant Examiner*—J. G. Mullins

[57] ABSTRACT

Certain substituted-4-hydroxy-(or 4-acyloxy-)2H-1,2-benzothiazine 1,1-dioxides having at the 3-position a 2-substituted-1,3,4-oxadiazol-5-yl, a 2-substituted-tetrazol-5-yl or a 1-substituted-tetrazol-5-yl group useful as selective 5-lipoxygenase pathway inhibitors; and methods for their preparation.

18 Claims, No Drawings

2H-1,2-BENZOTHIAZINE DERIVATIVES

BACKGROUND OF THE INVENTION

This invention relates to certain 1,2-benzothiazines which demonstrate selective 5-lipoxygenase (5-LO) pathway inhibitory activity. More particularly it relates to certain substituted-4-hydroxy- and 4-acyloxy-2H-1,2-benzothiazine 1,1-dioxides having at the 3-position a 2-substituted-1,3,4-oxadiazol-5-yl, a 2-substituted-tetrazol-5-yl or a 1-substituted-tetrazol-5-yl group.

Arachidonic acid is the biological precursor of a group of endogenous metabolites, the leukotrienes. Said metabolites arise via the action of arachidonate lipoxygenases and give rise to allergic reactions. 5-Lipoxygenase, for example, catalyzes the oxygenation of arachidonic acid at C.5. This is the first step in the biosynthesis of slow reacting substance of anaphylaxis (SRS-A), a bronchoconstrictive agent believed to cause allergic asthma in man.

Although discovery of the antiinflammatory activity of 1,2-benzothiazines has given rise to intensive investigation of said compounds, especially of the 1,1-dioxide derivatives thereof wherein the substituent at the 3-position is a substituted carboxamide, no one appears to have synthesized 1,2-benzothiazines having a heterocyclic moiety at the 3-position, or to have disclosed the use of 1,2-benzothiazines as inhibitors of 5-lipoxygenase.

The 5-LO inhibiting activity of several structural types of compounds is reported in the literature:

2,3,5-trimethyl-6-(12-hydroxy-5,10-dodecadiynyl)-1,4-benzoquinone (AA861), Yoshimoto et al., Biocnim. et Biophys. 713, 470–473 (1982) and analogs thereof;

5,6-methanoleukatriene derivatives including KCN-TEI-6172, and 5,8,11-eicosatriynoic acid (ETYA);

3-amino-1-(m-trifluoromethyl)phenyl-2-pyrazoline (BW 755c), Krishishara et al., FEBS Letters, 143, 13–16 (1982);

1-phenyl-3-pyrazolidone (Phenidone), Carty et al., Prostaglandins, 19, 671–679 (1980);

6,9-pyrroloprostacyclin (U-60,257), Bach et al., Prostaglandins, 23, 759–771 (1982); and tetrazole, acylhydroxylamine, hydroxymethylketone and amide derivatives of unsaturated fatty acids related to arachidonic acid, EP-104,468, published Apr. 14, 1984.

The overall medical significance of the problems of bronchoconstriction and pulmonary diseases gives rise to the need for selective and efficient inhibitors of 5-LO in order to prevent, or at least to minimize, the formation of SRS-A in man and, as a consequence, to reduce allergic asthma reactions.

SUMMARY OF THE INVENTION

The 5-LO inhibitors of this invention have formulae I and II

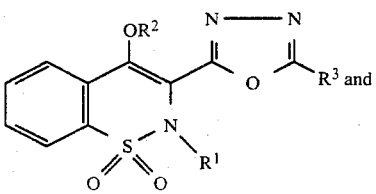

I

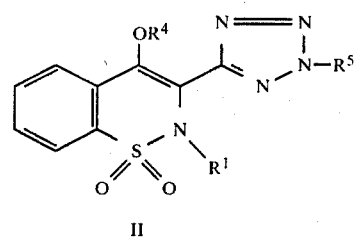

II wherein, in formula I, $R^1$ is alkyl having from 1 to 8 carbon atoms or —($CH_2$)$_m$—O—($CH_2$)$_n$O$R^6$ where m and n are each an integer from 1 to 4 and $R^6$ is alkyl having from one to six carbon atoms;

$R^2$ is hydrogen, alkanoyl having from 2 to 15 carbon atoms, cycloalkylcarbonyl having from 3 to 8 carbon atoms in the cycloalkyl moiety, benzoyl or benzoyl ring substituted with F, Cl, Br, I, $CF_3$, $CH_3$, $NO_2$ or $CH_3O$; and $R^3$ is alkyl having from 1 to 15 carbon atoms, thienyl, furyl, cycloalkyl having from 3 to 8 carbon atoms, phenyl or phenyl substituted with F, Cl, Br, I, $CF_3$, $CH_3$ or $CH_3O$; and wherein in formula II, $R^1$ is as defined above;

$R^4$ is hydrogen, alkanoyl having from 2 to 15 carbon atoms, benzoyl or benzoyl ring substituted with F, Cl, Br, I, $CF_3$, $CH_3$ or $CH_3O$; and $R^5$ is hydrogen, alkyl having from 1 to 15 carbon atoms, alkanoyl having from 2 to 15 carbon atoms, alkenyl, aralkenyl, cycloalkyl of from 3 to 8 carbon atoms, phenylethyl, cycloalkylcarbonyl having from 3 to 8 carbon atoms in the cycloalkyl moiety, benzoyl, benzoyl substituted with F, Cl, Br, I, $CF_3$, $CH_3$, $CH_3O$ or $NO_2$, furylmethyl, thienylmethyl, benzyl or benzyl ring substituted with F, Cl, Br, I, $CF_3$, $CH_3$, $NO_2$ or $CH_3O$.

Also included in this invention are the 1-(5-substituted isomers of formula II compounds; i.e., compounds wherein $R^5$ is attached to the 1-position of the tetrazolyl moiety.

Preferred compounds of the invention are those of formula I
wherein
$R^1$ is alkyl having from 1 to 4 carbon atoms or methoxyethoxymethyl;

$R^2$ is hydrogen, alkanoyl having from 2 to 15 carbon atoms, benzoyl, cyclohexylcarbonyl or methoxybenzoyl;

and $R^3$ is alkyl having from 7 to 15 carbon atoms, phenyl, methoxyphenyl, tolyl or cyclohexyl; and of formula II, wherein $R^1$ is alkyl having from 1 to 3 carbon atoms or methoxyethoxymethyl;

$R^4$ is hydrogen, acetyl or benzoyl; and $R^5$ is hydrogen, alkyl having 7 to 15 carbon atoms, benzyl, methylbenzyl or methoxybenzyl.

Of particular interest because of their potent and selective 5-LO inhibiting activity are those compounds of formula (I) wherein $R^1$ is alkyl having from 1 to 3 carbon atoms, $R^2$ is benzoyl, cyclohexylcarbonyl or acetyl; and $R^3$ is alkyl having from 9 to 11 carbon atoms, phenyl, methoxyphenyl or tolyl; and those compounds of formula (II) wherein $R^1$ is alkyl having from 1 to 3 carbon atoms, $R^4$ is acetyl, and $R^5$ is alkyl having from 8 to 10 carbon atoms, methoxybenzyl or methylbenzyl.

Particularly preferred compounds of formula I are those wherein $R^1$ is ethyl; $R^2$ is acetyl, cyclohexylcarbonyl, or benzoyl and $R^3$ is alkyl having from 7 to 11 carbon atoms, phenyl or tolyl. Particularly preferred compounds of formula II are those wherein $R^1$ is ethyl; $R^4$ is acetyl; and $R^5$ is alkyl having from 8 to 10 carbon atoms or methylbenzyl.

DETAILED DESCRIPTION OF THE INVENTION

The compounds of this invention are prepared from N-cyanomethylsaccharin [2-cyanomethyl-1,2-benzisothiazol-3(2H)-one 1,1-dioxide] by the abbreviated reaction sequence presented below:

However, in practice, molar ratios of from about 1:1.1 to 1:0.5 are favored. Methanol is generally used as solvent regardless of the alkali metal alkoxide used. The reaction is conducted at a temperature of below room temperature and preferably at from about 5°-10° C. in order to minimize side reactions.

The product (IV) is isolated by neutralization of the reaction mixture, desirably below room temperature, e.g. from 10°-15° C., and the precipitated solid recovered.

The second step involves alkylation of the sulfonamide moiety of (IV) with the appropriate halide, $R^1$—X, wherein X is iodo, chloro or bromo in the presence of an acid acceptor and in a reaction-inert solvent.

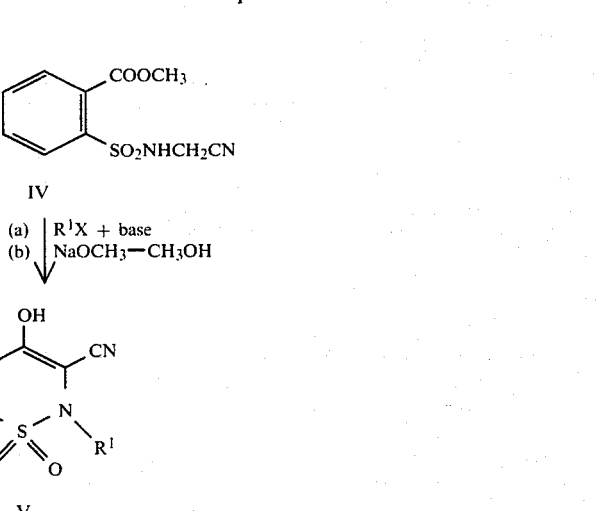

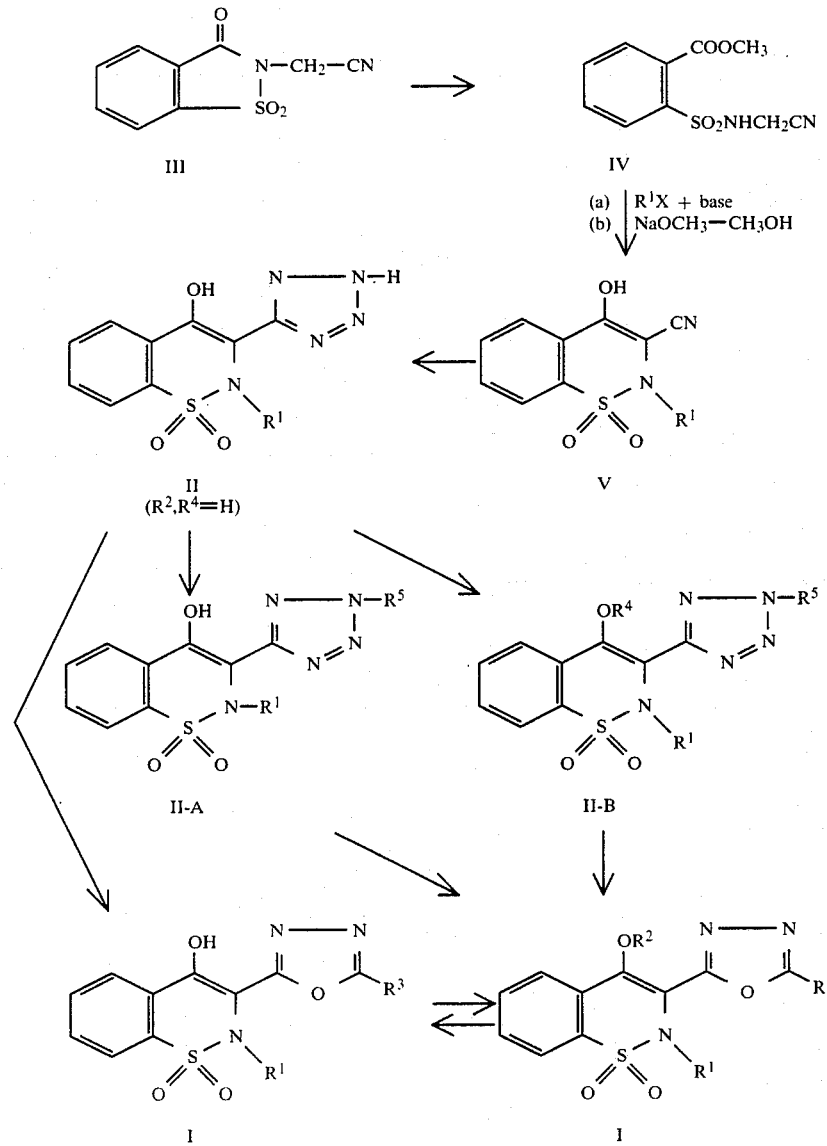

In the first step, N-cyanomethylsaccharin (III) is converted to o-carboalkoxy-N-cyanomethylbenzenesulfonamide (IV) by cleavage of the cyclic imide by reaction with an alkali metal alkoxide of 1-4 carbon atoms in a $C_{1-4}$ alkanol solvent. Sodium methoxide-methanol represents the preferred system for the cleavage reaction. In general, the molar ratio of cyclic imide to alkali metal alkoxide varies from about 1:1.5 to about 1:0.5. The molar ratio of said reactants is not critical.

The reactants are generally reacted together in stoichiometric or approximately stoichiometric amounts at a temperature of from about 25° to 5° C. Suitable reaction-inert solvents: i.e., those which do not react to any degree with the reactants and/or products in such a manner as to significantly reduce the yield of a given reaction. Representative of such solvents are acetone, water, N,N-dimethylformamide, methylene chloride, chloroform and mixtures thereof.

The choice of acid acceptor is somewhat dependent upon the solvent system used. It is desirable, in order to achieve optimum removal of by-product from the reaction, to use an acid acceptor which is soluble in the solvent system used. However, acid acceptors which are insoluble in the solvent can also be used. Aqueous systems are the more versatile systems in that both inorganic and organic acid acceptors can be used. When using a non-aqueous solvent system, tertiary amines, such as triethylamine, pyridine, N-methylmorpholine, N-ethylpiperidine and N,N-dimethylaniline are suitable acid acceptors. Aqueous systems permit use of the aforementioned bases and also of inorganic bases such as alkali metal hydroxides and carbonates. Inorganic bases can, of course, be used in non-aqueous solvents. For example, the inorganic bases enumerated above can be used as acid acceptors in N,N-dimethylformamide as those skilled in the art will recognize.

The compounds of formula (IV) and N-substituted derivatives of formula (IV) compounds can, if desired, be isolated by known procedures, or they can be converted to the cyclic compound of formula (V). It is generally preferred to at least obtain the formula (IV) compound in concentrated form before cyclizing it to a formula (V) compound.

The cyclization of formula (IV) compounds, (N-unsubstituted or N-substituted derivatives thereof), is readily accomplished by means of alkali metal $(C_{1-4})$alkoxide-$(C_{1-4})$alkanol and especially of sodium (or potassium) methoxide-methanol in a hydrocarbon solvent such as toluene, benzene, xylene, n-hexane at about room temperature. The cyclized formula (V) compounds are recovered by known procedures as by concentration of the reaction, addition of water to the concentrate followed by acidification thereof and removal of the product by filtration if precipitation thereof occurred, or by extraction with an appropriate water-immiscible solvent. Alternatively, the reaction is not concentrated but is extracted with water and the extracted then acidified.

Conversion of formula (V) compounds to the tetrazol-5-yl derivatives of formula (II) is accomplished by reaction of the cyano derivative, formula (V), with azide ion in the presence of an acid addition salt of ammonia or of amines and in a reaction inert solvent.

The azide ion can be derived from a variety of sources. The only criterion appears to be that the particular source chosen be capable of releasing azide ion under the conditions; i.e., solvent, temperature, of a given reaction. Suitable sources of azide ions are inorganic and organic azides. In the case of organic azides, the organic moiety must be strongly electron withdrawing in nature. Representative sources of azide ions are metal azides, especially alkali metal azides, trialkylsilyl azides having from one to four carbon atoms in each of the alkyl groups, such as trimethylsilyl azide and triethylsilyl azide, tetra-n-butylammonium azide, tetramethylguanidinium azide, hydrazoic acid, ammonium azide, trifluoromethylazide, N,N-dimethylanilinium azide, N-methyl-morpholinium azide and triethylammonium azide.

The molar ratio of azide to cyano reactant of formula (VI) is generally held in the range of from about 1:1 to about 6:1. Higher ratios can be used but are generally accompanied by reduced yields of the desired tetrazole product. In practice, molar ratios of 2:1 have been found to afford high yields of the desired tetrazol-5-yl compounds of formula (II).

The presence of from about 1 to about 5 moles of ammonium chloride or of acid addition salts of amines to azide reactant during the reaction is desirable. The acid addition salts of primary, secondary and tertiary amines can be used. The nature of the acid portion of the acid addition salt is immaterial to the operability of this process. However, certain acid addition salts are favored over others for such reasons as availability, ease of preparation and solubility in the reaction mixture. The suitablility of a given amine acid addition salt is easily determined by carrying out the process of this invention using the particular amine acid addition salt. Favored acid addition salts are the salts with mineral acids and organic acids such as alkane sulfonic acids such as methane and ethane sulfonic acids, p-toluenesulfonic acid, benzene-sulfonic acid naphthalenesulfonic acids, alkanoic acids such as acetic, n-butyric, octanoic, benzoic and substituted benzoic acids and cation exchange resins. The preferred amine acid addition salts are the hydrochloride salts of tertiary amines such as triethylamine, tri-n-propylamine, tri-n-butylamine, trimethylamine, N,N-dimethylaniline, N-methylpiperidine and N-methylmorpholine because of the satisfactory conversions of nitrile to tetrazole they afford in this process. Especially preferred is ammonium chloride.

Suitable reaction-inert solvents for this process are N,N-dimethyl formamide (DMF), halogenated hydrocarbons such as trichloroethanes, chloroform, and methylene chloride, ethers such as dioxane, tetrahydrofuran, dimethyl and diethyl ethers of ethyleneglycol and diethylene glycol, macrocyclic polyethers (crown compounds), benzene, xylene, tetralin and pyridine. DMF is a favored solvent in view of the favorable yields it affords and the ease of recovery of the tetrazolyl products therefrom.

In order to expedite the reaction the solvent should desirably be one which completely dissolves all reactants. As one skilled in the art appreciates, complete solubility is, however, not necessary. Partial solubility of reactants in the solvent system is sufficient to permit reaction to occur at an acceptable rate.

The reaction is generally conducted over the range of from about 20° C. to about 110° C. The favored temperature range is from about 25° C. to about 80° C. and the preferred range from about 40° C. to about 70° C. Temperature is not a critical factor and lower or higher temperatures can be employed. Lower temperatures, of course, require longer reaction times than do the higher temperatures. Temperatures above about 110° C. are usually avoided to minimize decomposition of reactants and products.

The reaction period depends in part upon the reactants and the solvent system used. As a general rule, the reaction is completed in periods ranging from about 2 to about 24 hours.

In the conversion of formula (V) to formula (II) compounds, the use of an acid rather than acid addition salts of ammonia or of amines also affords satisfactory reaction. Acids such as those enumerated above under acid addition salts of amines are representative of suitable acids.

The tetrazole compounds of formula (II) are converted to oxadiazoles of formula (I) via the Huisgen reaction. This reaction comprises acylation of the tetrazole (II) to produce a compound of formula (II-A) or (II-B). Said acylation is carried out under standard acylation conditions using the appropriate acid, acyl halide or acyl anhydride. Suitable solvents for the acylation reaction are aromatic hydrocarbons such as benzene, toluene or xylene; chlorinated hydrocarbons such as dichloromethane and chloroform. When the acylating agent is a liquid, e.g. acetic anhydride, it is advantageously used in excess to serve both as reactant and solvent. When isolation of the acyl derivative is desired, the reaction is conducted at temperatures ranging from about 5°–25° C. in order to avoid thermal fragmentation of the tretrazole derivative with loss of nitrogen and ultimate formation of a 1,3,4-oxadizole derivative.

Acylation with the appropriate acyl halide is carried out in the presence of an acid acceptor such as pyridine, triethylamine, N-methylmorpholine or N,N-dimethylaniline, at temperatures of from 5°–25° C., in a solvent such as those enumerated above. Alternatively, an excess of the acid acceptor, e.g. pyridine, can be used as solvent. Acylation with an acid is conducted in a solvent such as those enumerated above and in the presence of a dehydrative coupling agent such as dicyclohexylcarbodiimide according to known procedures.

The acylation products are isolated, if desired, by conventional methods as by filtration or, if no solid forms, by concentration of the reaction mixture to an oil. In many instances the oily product obtained can be obtained as a solid, or as crystals, by addition of n-hexane or other solvent. When an acyl halide is used as acylating agent in the presence of an excess of acid acceptor, the products are conveniently recovered by diluting the reaction mixture with aqueous acid, e.g. dilute hydrochloric acid, and removal of the solid product by filtration. When excess acid acceptor is not used, dilution of the reaction mixture with an organic solvent and extraction of the resulting solution with aqueous acid (e.g. dilute HCl) and water affords the acylated product.

Mono- or diacylated products are produced depending upon the stoichiometric ratio of acylating agent to tetrazole reactant of formula (II). The use of up to one equivalent of acylating agent per mole of formula (II) compound affords the monoacyl derivative as principal product. Greater amounts of acylating agent favor diacylation; i.e., at the 4-hydroxy group and at the tetrazolyl group. The use of two or more equivalents, of course, favors diacylation.

An alternative procedure for acylating formula (II) compounds comprises reacting said compounds with the appropriate carboxylic acid in the presence of a dehydrative coupling agent such as a carbodiimide, ethoxyacetylene, alpha-chlorovinyl ethyl ether, N,N'-carbonyldiimidazole, N-hydroxysuccinimide and 2-ethyl-5-(3-sulfophenyl)-1,2-oxazole-betaine. Preferred as coupling agent is dicyclohexylcarbodiimide. Said dehydrative coupling agents when used to prepare acylated products of this invention are used according to standard procedures. For example, the formula (II) compound and appropriate acid are reacted in a reaction-inert solvent such as toluene or xylene, at the reflux temperature in the presence of dicyclohexylcarbodiimide. To insure satisfactory yields excesses of carbodiimide and acid, based on the formula (II) compound, are used. In practice mole ratios of formula (VIII) compound to acid to dicyclohexylcarbodiimide of 1:3:3 have been found satisfactory.

The 4-acyl derivatives of compounds of formula (I) are readily converted to the corresponding 4-hydroxy derivatives by alkaline hydrolysis, especially by use of alkali metal alkoxides in an alkanol solvent corresponding to the alkanol from which the alkoxide is derived. The hydrolysis occurs at room temperature. The 4-hydroxy derivative is recovered by removal of the solvent and adjustment of the pH of an aqueous mixture of the residue to about 1.5.

The 4-hydroxy formula (I) compounds thus obtained can then be reacylated with a different acylating agent, if desired. The reacylation is carried out according to the conditions described above.

The isolated compounds of formula (II-B) are transformed to formula (I) compounds by heating to an elevated temperature, e.g. from 80°–150° C., in a reaction-inert solvent such as toluene, benzene, xylene, acyl anhydride (excess). Lower temperatures require too large a heating period to be practical. Higher temperatues can, of course, be used but afford no advantage. The oxadizole compounds are recovered by concentration of the reaction mixture, cooling the concentrate to precipitate a solid which is filtered off.

The acylation products of formula (II-B) need not be isolated prior to converting them to oxadiazoles of formula (I). The conversion of formula (II) to formula (I) compounds can be carried out in situ without isolation of the intermediate compounds of formula (II-B). The reaction comprises acylating the tetrazole of formula (II), generally with excess acylating agent, e.g. from 2–5 fold excess, over that required to produce the diacyl derivative at an elevated temperature. The same acylating agents and solvent systems as discussed above in connection with the conversion of formula (II) to formula (I) compounds with isolation of the formula (II-B) intermediates are used in this one step conversion. The one difference is the temperature of the acylation process which should be carried out at from 80°–150° C. to achieve acylation with direct transformation to formula (I) compounds.

Compounds of formula II-A and B wherein $R^5$ is benzyl, methoxybenzyl or methylbenzyl are prepared from formula (II) compounds by reaction of said formula (II) compound with the appropriate aralkyl halide such as benzyl bromide, 2-methoxybenzyl chloride and 4-methylbenzyl chloride, in a reaction-inert solvent in the presence of an acid acceptor. It is preferred to use an aralkyl bromide as reactant. When an aralkyl chloride is used as reactant, it is advantageous to add a small amount of alkali metal iodide as accelerator because of the relatively lower reactivity of aralkyl chlorides compared to aralkyl bromides.

Suitable solvents are N,N-dimethylformamide, N,N-diethylformamide, N-methyl-2-pyrrolidone, dimethylsulfoxide, toluene and xylene. The reaction is conducted at ambient temperature until complete or substantially complete. Potassium carbonate is favored as acid acceptor when N,N-dimethylformamide is used as solvent. However, other acid acceptors, inorganic and organic in nature, such as sodium carbonate, alkali metal hydrides or alkoxides; tertiary amines such as pyridine, triethylamine, N-methylmorpholine can also be used. The products are isolated by known procedures as, for example, by dilution with water or dilute aqueous acid followed by filtration of the product. A mixture of the 2-aralkyl and 1-aralkyl isomers is generally obtained. The isomers are separated by taking advantage of their solubility differences.

The 5-LO inhibiting activity of the compounds of this invention is tested by a cell culture assay which determines the effect of said compounds on the metabolism of arachidonic acid and, therefore, their ability to inhibit the activity of 5-LO. The procedure is described by Jakschick et al., Prostaglandins 16, 733–748 (1978).

Because of their 5-LO inhibiting activity, the compounds of formulae I and II are effective agents for the prophylactic and therapeutic treatment of bronchoconstrictive and pulmonary diseases in man. When used for this purpose, said compounds are administered via the oral, parenteral or topical routes. The compounds may be administered per se but are preferably administered in the form of a composition, that is, in combination with a pharmaceutically acceptable carrier, which compositions may also comprise excipients, flavors, adjuvants, etc. in keeping with good pharmaceutical practice. The compositions may be in the form of solid, semi-solid or liquid dosage forms; such as, for instance, tablets, capsules, pills, powders, suppositories, solutions, elixirs, syrups, suspensions, creams, lozenges, pastes and sprays. As those skilled in the art recognize, the chosen route of administration of the herein described 5-LO inhibitors determines the form of composition to be used. In general, it is preferred to use a unit dosage form of the herein described inhibitors in order to achieve ease of treatment and administration of precise doses of the active compound. In general, the therapeutically effective compounds of this invention are present in such dosage forms at concentration levels ranging from about 0.5% to about 90% by weight of the total composition; i.e., in amount sufficient to provide the desired unit dose.

The 5-LO inhibitor compounds of this invention may be administered in single or multiple doses. The particular route of administration and the dosage regimen will be determined by the attending physician in keeping with the condition of the individual to be treated and said individual's response to the treatment. In general, for oral administration, doses of from about 10 mg to about 1000 mg per day in single or multiple doses are sufficient. For parenteral administration, doses of from about 5 mg to 750 mg per day are used in single or multiple doses. In some instances, dosage levels below the lower limit of the aforesaid range may be more than adequate, while in other cases still larger doses may be employed without causing any harmful or deleterious side effects to occur provided that such higher dose levels are first divided into several smaller doses that are to be administered throughout the day.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium sterate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes, and, if so desired, emulsifying and/or suspending agents as well, together with such diluents as water, ethanol, propylene glycol, glycerin and various like combinations thereof.

For purposes of parenteral administration, solutions in either sesame or peanut oil or in aqueous propylene glycol may be employed, as well as sterile aqueous solutions of the corresponding water-soluble alkali metal or alkaline-earth metal salts previously enumerated. Such aqueous solutions should be suitably buffered if necessary and the liquid diluent first rendered isotonic with sufficient saline or glucose. These particular solutions are especially suitable for intravenous, intramuscular and subcutaneous injection purposes. Additionally, it is also possible to administer the aforesaid compounds topically and this may be preferably done by way of creams, salves, jellies, pastes, ointments and the like, in accordance with standard pharmaceutical practice.

This invention is still further illustrated by the following examples, which are not to be construed as imposing limitations upon the scope thereof. On the contrary, it is to be clearly understood that resort may be had to various other embodiments, modifications and equivalents thereof which readily suggest themselves to those skilled in the art without departing from the spirit of the present invention and/or the scope of the appended claims.

EXAMPLE 1

4-Hydroxy-2-methyl-3-(tetrazol-5-yl)-1,2-benzothiazine 1,1-Dioxide Hemihydrate

A mixture of 3-cyano-4-hydroxy-2-methyl-1,2-benzothiazine 1,1-dioxide (11.8 g), sodium azide (3.9 g) and ammonium chloride (3.2 g) in dimethylformamide (100 ml) was heated at 60°–70° C. for 12 hours under nitrogen. The resulting mixture was poured into a mixture of water (400 ml), 6N HCl (30 ml) and ice (100 g) with stirring and the solid filtered off to give an off-white color product in 85% yield. Pure compound was obtained in 90% yield by dissolving the compound (3.53 g) in 0.5N NaOH (400 ml), treating with activated carbon (1.0 g) and adjusting pH to 2 with 6N HCl.

M.P.: 227° C. (dec.).

IR (KBr): 1610, 1570, 1345, 1335, 1180 cm$^{-1}$.

NMR (Acetone d$_6$): 83.06 (s, 3H, N—CH$_3$), 7.7–8.4 (m).

Mass (EI): m/e 279 (M), 215 (M—SO$_2$), 186 (M—SO$_2$N$_2$).

Analysis Calculated for C$_{10}$H$_9$N$_5$O$_3$S.½H$_2$O: C, 41.66; H, 3.50, N, 24.29%. Found: C, 41.63; H, 3.46; N, 23.94%.

In like manner the products of Preparations 4 and 5 are converted to the following compounds, respectively:

(a) 2-ethyl-4-hydroxy-3-(tetrazol-5-yl)-1,2-benzothiazine 1,1-dioxide in 86% yield:

M.P.: 214° C.

IR (KBr): 1615, 1570, 1340, 1175 cm$^{-1}$.

NMR (Acetone d$_6$): 0.79 (t, 3H), 3.58 (q, 2H), 7.8–8.4 (m); and (b) 4-hydroxy-2-(2-methoxyethoxymethyl)-3-(tetrazol-5-yl)-1,2-benzothiazine 1,1-dioxide in 71.3% yield:

M.P. (from acetone): 180°–181.0° C.

IR (KBr): 1610, 1565, 1350, 1185 cm$^{-1}$.

NMR (CDCl$_3$): 3.82 (s, 3H), 3.8–4.3 (m, 4H), 4.96 (W, 3H), 7.6–8.4 (m).

(c) 4-hydroxy-2-(n-propyl)-3-(tetrazol-5-yl)-1,2-benzothiazine 1,1-dioxide:

M.P.: 181°–183° C.

IR (KBr): 1610, 1550, 1340, 1180 cm$^{-1}$.

NMR (DMSO-d$_6$): 0.52 (t, J=Hz, 3H), 1.05 (m, 2H), 3.56 (t, J=7 Hz, 2H), 7.5-8.5 (m, 4H).

(d) 4-hydroxy-2-isopropyl-3-(tetrazol-5-yl)-1,2-benzothiazine 1,1-dioxide:

M.P.: 220°-222° C.

IR (KBr): 1620, 1575, 1330, 1180 cm$^{-1}$.

NMR (DMSO-d$_6$): 0.96 (d, J=7 Hz, 6H), 4.00 (m, 1H), 7.6-8.4 (m, 4H).

EXAMPLE 2

4-Hydroxy-2-methyl-3-(2-methyl-1,3,4-oxadiazol-5-yl)-1,2-benzothiazine 1,1-Dioxide (a) 4-Acetoxy-2-methyl-3-(2-acetyltetrazol-5-yl)-1,2-benzothiazine 1,1-dioxide A mixture of the title tetrazole of Example 1 (2.75 g) in acetic anhydride (30 ml) was stirred at room temperature for 16 hours. The resulting crystals were filtered off, washed with ether and dried in vacuo to give the title diacetyl derivative, 2.35 g. The filtrate was concentrated at 40° C. and triturated with dichloroethane to afford further product 0.75 g. Combined yield was 3.10 g (89%).

M.P.: 164° C. (dec.)

IR (KBr): 1800, 1770, 1350, 1170 cm$^{-1}$.

NMR (DMSO, d$_6$): 1.94 (s, 3H, O—COCH$_3$), 2.50 (s, 3H, N—COCH$_3$), 3.08 (s, 3H, N—CH$_3$), 7.8-8.2 (m).

Mass (EI): m/e 293 (M—C$_2$H$_2$O—N$_2$), 229 (293—SO$_2$).

Analysis Calculated for C$_{14}$H$_{13}$N$_3$O$_5$S: C, 46.28; H, 3.61; N, 19.28%. Found: C, 46.37; H, 3.55; N, 19.03%.

(b) 4-Acetoxy-2-methyl-3-(2-methyl-1,3,4-oxadiazol-5-yl)-1,2-benzothiazine 1,1-dioxide A suspension of the product of (a) above (3.60 g), in toluene (40 ml) was refluxed for 2 hours, and the resulting solution concentrated to half volume and cooled to room temperature to give crystals. Filtration followed by drying in vacuo afforded colorless crystals, 3.29 g, in 99.1% yield of product (b).

M.P.: 188.0°-189.5° C.

IR (KBr): 1785, 1350, 1180 cm$^{-1}$.

NMR (CDCl$_3$): 2.68 (s, 3H), 3.07 (s, 3H, N—CH$_3$), 7.65-8.4 (m).

Mass (EI): m/e 293 (M—CH$_2$CO), 229 (293—SO$_2$).

(c) 4-Hydroxy-2-methyl-3-(2-methyl-1,3,4-oxadiazol-5-yl)-1,2-benzothiazine 1,1-dioxide To a solution of product (b) (2.218 g) in methanol (20 ml) was added 28% sodium methoxide (1.28 ml). After stirring at room temperature for 30 minutes, the solvent was stripped off and water (30 ml) was added. With vigorous stirring the pH was adjusted to ca. 1.5 with 6N HCl and the resulting solid granulated for 1 hour, filtered off, washed with water, and dried in vacuo to give compound (c), 1.903 g, 98% yield.

M.P.: 226°-227° C.

IR (KBr): 1340, 1170

NMR (CDCl$_3$): 2.68 (s, 3H), 3.07 (s, 3H), 7.65-8.30 (m, 4H)

Mass (EI): m/e 293 (M), 229 (M—SO$_2$).

Analysis Calculated for C$_{12}$H$_{11}$N$_3$O$_4$S: C, 49.10; H, 3.78; N, 14.33%. Found: C, 49.01; H, 3.83; N, 14.30%.

EXAMPLE 3

4-Decanoyloxy-2-methyl-3-(2-nonyl-1,3,4-oxadiazol-5-yl)-1,2-benzothiazine 1,1-Dioxide A mixture of 4-hydroxy-2-methyl-3-(tetrazol-5-yl)-1,2-benzothiazine 1,1-dioxide hemihydrate (1.80 g) (6.25 mmoles) and decanoic anhydride (12 g) in toluene (20 ml) was refluxed for 16 hours. The solvent was stripped to dryness and the residue recrystallized from toluene (25 ml) to give the title compound in 68.4% yield.

M.P.: 68°-69° C. (n-hexane).

IR (KBr): 1780, 1355 cm$^{-1}$.

NMR(CDCl$_3$): 0.6-2.1 (m), 2.78 (t, 2H), 2.90 (t, 2H), 3.15 (s, 3H), 7.5-8.1 (m).

Analysis Calculated for C$_{30}$H$_{45}$N$_3$O$_5$S: C, 64.37; H, 8.10; N, 7.50%. Found: C, 64.42; H, 7.97; N, 7.38%.

EXAMPLE 4

4-Hydroxy-2-methyl-3-(2-nonyl-1,3,4-oxadiazol-5-yl)-1,2-benzothiazine 1,1-Dioxide To a solution of the title compound of Example 3 (4.11 g) in methanol (20 ml) was added 28% sodium methoxide (1.28 ml). After stirring at room temperature for 30 minutes, the solvent was stripped off and water (30 ml) added. With vigorous stirring the pH was adjusted to ca. 1.5 by addition of 6N HCl and the resulting solid granulated for 1 hour at 20° C. It was removed by filtration, washed with water and dried in vacuo to give the title compound in 63% yield.

M.P.: 61.5°-62.0° C. (n-hexane).

IR (KBr): 1540, 1360 cm$^{-1}$.

NMR(CDCl$_3$): 0.8-2.2 (m), 2.98 (t, J=7, 2H), 3.05 (s, 3H), 7.6-8.4 (m).

Analysis Calculated for C$_{20}$H$_{27}$N$_3$O$_4$S: C, 59.23; H, 6.71; N, 10.36%. Found: C, 59.18; H, 6.75; N, 10.31%.

EXAMPLE 5

4-Benzoyloxy-2-methyl-3-(2-methyl-1,3,4-oxadiazol-5-yl)-1,2-benzothiazine 1,1-Dioxide To a solution of 4-hydroxy-2-methyl-3-(2-methyl-1,3,4-oxadiazol-5-yl)-1,2-benzothiazine 1,1-dioxide, (0.155 g) in pyridine (0.5 ml) was added benzoyl chloride (0.63 ml) at 5°-10° C. After being stirred at room temperature for 1 hour, the mixture was diluted with dichloromethane, washed successively with dilute HCl, water and dilute sodium bicarbonate solution and dried over sodium sulfate to give, on concentration, crude solids 0.213 g. Recrystallization from toluene gave the title compound 0.156 g (74%).

M.P.: 196°-197° C.

IR (KBr): 1745, 1350 cm$^{-1}$.

NMR(CDCl$_3$): 2.42 (s, 3H), 3.30 (s, 3H), 7.2-8.5 (m).

Analysis Calculated for C$_{29}$H$_{15}$N$_3$O$_5$S: C, 57.42; H, 3.80; N, 10.57%. Found: C, 57.72; H, 3.92; N, 10.40%.

EXAMPLE 6

4-Benzoyloxy-2-methyl-3-(2-methyl-1,3,4-oxadiazol-5-yl)-1,2-benzothiazine 1,1-Dioxide To a suspension of 4-hydroxy-2-methyl-3-(tetrazol-5-yl)-1,2-benzothiazine 1,1-dioxide hemihydrate (2.88 g) in pyridine (10 ml) was added dropwise benzoyl chloride (1.02 ml) at 5°-10° C. After being stirred at room temperature for 1 hour, the mixture was poured into 0.6N HCl (200 ml) with vigorous stirring. The resulting solids were collected by filtration and washed with water. The solids were dissolved in dichloromethane (100 ml), washed with water and dried over sodium sulfate to give crude 4-benzoyloxy-2-methyl-3-(tetrazol-5-yl)-1,2-benzothiazine 1,1-dioxide, 4.24 g.

The crude product (0.205 g) was refluxed in acetic anhydride (5 ml) for 1 hour then concentrated under reduced pressure. Crystallization of the residue thus produced from toluene gave 0.067 g of title product identical to that of Example 5.

EXAMPLE 7

3-(2-Cyclohexyl-1,3,4-oxadiazol-5-yl)-4-cyclohexylcarbonyloxy-2-methyl-1,2-benzothiazine 1,1-Dioxide A mixture of 4-hydroxy-2-methyl-3-(tetrazol-5-yl)-1,2-benzothiazine 1,1-dioxide hemihydrate (0.72 g), cyclohexane-carboxylic acid (0.96 g) and N,N'-dicyclohexylcarbodiimide (1.55 g) in xylene (15 ml) was refluxed for 3 hours. The mixture was cooled, filtered and the filtrate diluted with dichloromethane (50 ml). The solution was washed with saturated sodium bicarbonate solution, then with water and dried over sodium sulfate. The solvent was replaced by toluene and resulting solid (Urea) was removed by filtration. The filtrate was concentrated and the residue crystallized from methanol to give 0.492 g (42%) of the title product.

M.P.: 175°–177° C. (n-hexane and toluene).
IR (KBr): 1770, 1360 cm$^{-1}$.
NMR(CDCl$_3$): 1.0–3.2 (m), 3.18 (s, 3H), 7.4–8.2 (m).
Analysis Calculated for C$_{24}$H$_{29}$N$_3$O$_5$S: C, 61.13; H, 6.20; N, 8.91%. Found: C, 60.98; H, 6.17; N, 8.90%.

EXAMPLE 8

4-Hydroxy-2-methyl-3-(2-phenyl-1,3,4-oxadiazol-5-yl)-1,2-benzothiazine 1,1-Dioxide and
4-Benzoyloxy-2-methyl-3-(2-phenyl-1,3,4-oxadiazol-5-yl)-1,2-benzothiazine 1,1-Dioxide A mixture of 4-hydroxy-2-methyl-3-(tetrazol-5-yl)-1,2-benzothiazine 1,1-dioxide (0.576 g) and benzoic anhydride (1.81 g) in toluene (15 ml) was refluxed for 16 hours, then concentrated to a viscous oil which was solidified in n-hexane (10 ml) and filtered. The resulting solid and filtrate were treated separately. The solid was submitted to silica gel column chromatography (SiO$_2$, 20 g) and eluted with a mixed solvent (dichloromethane and ethylacetate 5:1) to give 0.420 g (45.8%) of the title benzoyl derivative.

M.P.: 178°–179° C. (toluene).
IR (KBr): 1745, 1355 cm$^{-1}$.
NMR(CDCl$_3$): 3.38 (s, 3H), 7.2–8.8 (m).
Analysis Calculated for C$_{24}$H$_{17}$N$_3$O$_5$S.$\frac{1}{2}$ toluene: C, 65.33; H, 4.19; N, 8.31%. Found: C, 65.12; H, 4.25; N, 8.40%.

The above-mentioned filtrate was concentrated to an oil, and methanol (20 ml) and 28% sodium methoxide in methanol (2 ml) were added. After being stirred for 16 hours, the mixture was concentrated, acidified with 6N HCl and filtered. The solids were recrystallized from benzene to give 0.231 g (32.5%) of the title 4-hydroxy compound.

M.P.: 257° C.
IR (KBr): 1610, 1535, 1345 cm$^{-1}$.
NMR(CDCl$_3$): 3.16 (s, 3H), 7.4–8.4 (m).
Analysis Calculated for C$_{24}$H$_{17}$N$_3$O$_5$S.$\frac{1}{2}$ toluene: C, 65.33; H, 4.19; N, 8.31%. Found: C, 65.12; H, 4.25; N, 8.40%.

EXAMPLE 9

4-Benzoyloxy-2-ethyl-3-(2-phenyl-1,3,4-oxadiazol-5-yl)-1,2-benzothiazine 1,1-Dioxide and
4-Hydroxy-2-ethyl-3-(2-phenyl-1,3,4-oxadiazol-5-yl)-1,2-benzothiazine 1,1-Dioxide Following the procedure of Example 8 but using stoichiometric amounts of 4-hydroxy-2-ethyl-3-(tetrazol-5-yl)-1,2-benzothiazine 1,1-dioxide as reactant in place of the corresponding 2-methyl derivative of Example 8 afforded the title 4-benzoyl derivative in 39% yield and the title 4-hydroxy derivative in 22.2% yield.

4-Benzoyl derivative:
M.P.: 117°–118° C. (toluene).
IR (KBr): 1755, 1350 cm$^{-1}$.
NMR(CDCl$_3$): 1.02 (t, J=7, 3H), 4.02 (q, J=7, 2H), 7.1–8.6 (m).
Analysis Calculated for C$_{25}$H$_{19}$N$_3$O$_5$S: C, 65.88; H, 4.45; N, 8.09%. Found: C, 65.34; H, 4.39; N, 8.20%.

4-Hydroxy compound:
M.P.: 214°–216° C. (toluene).
IR (KBr): 1610, 1530, 1350 cm$^{-1}$.
NMR(CDCl$_3$): 0.95 (t, J=7, 3H), 3.73 (q, J=7, 2H), 7.4–8.3 (m).
Analysis Calculated for C$_{18}$H$_{15}$N$_3$O$_5$S: C, 58.52; H, 4.09; N, 11.38%. Found: C, 58.41; H, 4.07; N, 11.36%.

EXAMPLE 10

4-Benzoyloxy-2-(2-methoxyethoxymethyl)-3-(2-phenyl-1,3,4-oxadiazol-5-yl)-1,2-benzothiazine 1,1-Dioxide and
4-Hydroxy-2-(2-methoxyethoxymethyl)-3-(2-phenyl-1,3,4-oxadiazol-5-yl)-1,2-benzathiazine 1,1-Dioxide Repetition of the procedure of Example 8, but using 4-hydroxy-2-(2-methoxyethoxymethyl)-3-(tetrazol-5-yl)-1,2-benzathiazine 1,1-dioxide as reactant in place of the 2-methyl derivative of said Example afforded the title compounds:

4-Benzoyl derivative in 43% yield:
M.P.: 128°–129° C.
IR (KBr): 1750, 1350 cm$^{-1}$.
NMR(CDCl$_3$): 3.15 (s, 3H), 3.1–3.5 (m, 4H), 5.55 (s, 2H), 7.1–8.6 (m).
Analysis Calculated for C$_{27}$H$_{23}$N$_3$O$_7$S: C, 60.78; H, 4.34; N, 7.88%. Found: C, 60.50; H, 4.20; N, 7.92%.

4-Hydroxy compound in 13.5% yield:
M.P.: 156°–163° C.
IR (KBr): 1610, 1540, 1350 cm$^{-1}$.
NMR(CDCl$_3$): 3.15 (s, 3H), 3.0–3.5 (m, 4H), 5.25 (s, 2H), 7.4–8.4 (m).

EXAMPLE 11

4-Benzoyloxy-3-(2-cyclohexyl-1,3,4-oxadiazol-5-yl)-2-methyl-1,2-benzothiazine 1,1-Dioxide (a) 3-(2-Cyclohexyl-1,3,4-oxadiazol-5-yl)-4-hydroxy-2-methyl-1,2-benzothiazine 1,1-dioxide The product of Example 7 was hydrolyzed according to the procedure of Example 4 to give the above-named hydroxy derivative in 90% yield.

M.P.: 184°–185.0° C.
IR (KBr): 1530, 1345 cm$^{-1}$.
NMR(CDCl$_3$): 1.1–2.5 (m), 3.05 (s, 3H), 7.6–8.4 (m).

(b) Benzoylation of compound (a):

The hydroxy compound (a) was benzoylated according to the procedure of Example 5 to give the title compound in 91% yield:

M.P.: 157° C.
IR (KBr): 1755, 1355, 1235 cm$^{-1}$.
NMR(CDCl$_3$): 0.7–2.4 (m, 10H), 2.5–3.1 (m, 1H), 3.55 (s, 3H), 7.2–8.6 (m).
Analysis Calculated for C$_{24}$H$_{23}$N$_3$O$_5$S: C, 61.92; H, 4.98; N, 9.03%. Found: C, 61.76; H, 4.97; N, 9.00%.

EXAMPLE 12

4-Hydroxy-2-methyl-3-[2-(2-methoxyphenyl)-1,3,4-oxadiazol-5-yl]-1,2-benzothiazine 1,1-Dioxide (a) 4-(2-Methoxybenzoyloxy)-3-[2-(2-methoxyphenyl)-1,3,4-oxadiazol-5-yl]-2-methyl-1,2-benzothiazine 1,1-dioxide A mixture of 4-hydroxy-2-methyl-3-(tetrazol-5-yl)-1,2-benzothiazine 1,1-dioxide (0.72 g), o-anisic acid (1.14 g) and N,N'-dicyclohexylcarbodiimide (1.55 g) in xylene (15 ml) was refluxed for 3 hours, then cooled to 20° C. Needle crystals which formed were removed by filtration and the filtrate was diluted with dichloromethane, washed with saturated sodium bicarbonate solution and dried over sodium sulfate. Removal of the solvent in vacuo gave a solid residue which was crystallized from methanol to give 0.983 g (75.8%) of the ester derivative.

M.P.: 119°–120° C. ($CH_3OH$).

IR (KBr): 1750, 1600, 1350, 1180 $cm^{-1}$.

NMR($CDCl_3$): 3.40 (s, 3H), 3.81 (s, 3H), 3.86 (s, 3H), 6.8–8.4 (m).

(b) Hydrolysis of compound (a) to produce the title compound.

The ester derivative of (a) was treated with sodium methoxide according to the procedure of Example 4 to give the title compound in 94% yield.

M.P.: 213°–214° C. (toluene).

IR (KBr): 1605, 1535, 1355, 1190 $cm^{-1}$.

NMR($CDCl_3$): 3.16 (s, 3H), 4.03 (s, 3H), 6.9–8.4 (m).

EXAMPLE 13

4-Benzoyloxy-2-methyl-3-[2-(2-methoxyphenyl)-1,3,4-oxadiazol-5-yl]-1,2-benzothiazine 1,1-Dioxide Following the procedure of Example 5, 4-hydroxy-2-methyl-3-[2-(2-methoxyphenyl)-1,3,4-oxadiazol-5-yl]-1,2-benzothiazine 1,1-dioxide, the product of Example 12, was benzoylated to give the title compound in 74% yield.

M.P.: 198°–199° C. (toluene).

IR (KBr): 1755, 1355, 1240 $cm^{-1}$.

NMR($CDCl_3$): 3.40 (s, 3H), 3.88 (s, 3H), 6.7–8.5 (m).

Analysis Calculated for $C_{25}H_{19}N_3O_6S$: C, 61.34; H, 3.91; N, 8.88%. Found: C, 61.62; H, 3.99; N, 8.46%.

EXAMPLE 14

2-Methyl-3-(2-phenyl-1,3,4-oxadiazol-5-yl)-4-propionyloxy-1,2-benzothiazine 1,1-Dioxide Following the procedures of Example 5, but substituting propionyl chloride for benzoyl chloride, 4-hydroxy-2-methyl-3-(2-phenyl-1,3,4-oxadiazol-5-yl)-1,2-benzothiazine 1,1-dioxide was acylated to give the title product.

M.P.: 143°–146° C.

IR (KBr): 1780, 1360 $cm^{-1}$.

NMR($CDCl_3$): 1.35 (t, 3H), 2.90 (q, 2H), 3.28 (s, 3H), 7.5–8.4 (m).

EXAMPLE 15

4-Benzoyloxy-3-(2-ethyl-1,3,4-oxadiazol-5-yl)-2-methyl-1,2-benzothiazine 1,1-Dioxide (a) Following the procedure of Example 4, 2-methyl-3-(2-ethyl-1,3,4-oxadiazol-5-yl)-4-propionyloxy-1,2-benzothiazine 1,1-dioxide was hydrolyzed to the corresponding 4-hydroxy derivative in 96.3% yield.

M.P.: 179° C.

IR (KBr): 1345, 1180 $cm^{-1}$.

NMR($CDCl_3$): 1.48 (t, J=7 Hz, 3H), 3.03 (q, J=7 Hz, 2H), 3.08 (s, 3H), 7.6–8.4 (m, 4H).

Mass (EI): m/e 307 ($M^+$), 243 ($M-SO_2$).

Analysis Calculated for $C_{13}H_{13}N_3O_4S$: C, 50.80; H, 4.26; N, 13.67%. Found: C, 50.68; H, 4.26; N, 13.61%.

(b) The 4-hydroxy compound of step (a) was benzoylated according to the procedure of Example 6 to give the title product in 72% yield.

M.P.: 191°–192.5° C. (toluene).

IR (KBr): 1750, 1350 $cm^{-1}$.

NMR($CDCl_3$): 1.18 (t, J=7 Hz, 3H), 2.75 (q, J=7 Hz, 2H), 3.31 (s, 3H), 7.2–8.5 (m).

EXAMPLE 16

4-Acetoxy-3-(2-benzyltetrazol-5-yl)-2-methyl-1,2-benzothiazine 1,1-Dioxide (a) 3-(2-Benzyltetrazol-5-yl)-4-hydroxy-2-methyl-1,2-benzothiazine 1,1-dioxide To a mixture of 4-hydroxy-2-methyl-3-(tetrazol-5-yl)-1,2-benzothiazine, 1,1-dioxide hemihydrate (2.88 g) and potassium carbonate (0.69 g) in dimethylformamide (10 ml) was added benzylbromide (1.80 g) and stirring was continued for 16 hours. The mixture was poured into 0.15N HCl (75 ml), and the resulting solid collected by filtration, washed with water, and then with n-hexane to give crude product (3.59 g) which was recrystallized from toluene to give colorless crystals, 2.81 g (74.4%).

M.P.: 135°–136.0° C.

IR (KBr): 1620, 1610, 1340, 1180 $cm^{-1}$.

NMR($CDCl_3$): 3.09 (s, 3H), 5.80 (s, 2H), 7.48 (s, 5H), 7.6–8.4 (m).

Analysis Calculated for $C_{17}H_{15}N_5O_3S$: C, 55.27; H, 4.09; N, 18.96%. Found: C, 55.16; H, 4.16; N, 18.77%.

(b) Acylation of compound (a):

A mixture of compound (a) above (0.30 g) and acetic anhydride (5 ml) was refluxed for 4 hours and then concentrated. The residual oil solidified upon addition of n-hexane. After removal of the solvent by decantation, the solid was crystallized from toluene, filtered off and dried in vacuo to give 0.275 g (90.5%) of the title compound.

M.P.: 173° C.

IR (KBr): 1780, 1350 $cm^{-1}$.

NMR($CDCl_3$): 2.34 (s, 3H), 3.22 (s, 3H), 5.85 (s, 2H), 7.3–8.1 (m).

Analysis Calculated for $C_{19}H_{19}N_5O_4S$: C, 55.46; H, 4.17; N, 17.02%. Found: C, 55.71; H, 4.20; N, 17.04%.

EXAMPLE 17

4-Benzoyloxy-3-(2-benzyltetrazol-5-yl)-2-methyl-1,2-benzothiazine 1,1-Dioxide

A mixture of the product of Example 16 (a) (0.6 g) and benzoic anhydride (1.20 g) in xylene (20 ml) was refluxed for 12 hours then concentrated to a viscous oil, which was dissolved in dichloromethane (50 ml) and washed with 20% NaOH aqueous solution to remove starting material. The organic layer was washed with water, dried over sodium sulfate and concentrated to give a solid which was recrystallized from toluene to afford 0.587 g (83.1%) of the title product.

M.P.: 186°–187° C.

IR (KBr): 1760, 1350 $cm^{-1}$.

NMR($CDCl_3$): 3.29 (s, 3H), 5.62 (s, 2H), 7.0–8.5 (m).

Analysis Calculated for $C_{24}H_{19}N_5O_4S$: C, 60.87; H, 4.04; N, 14.79%. Found: C, 61.00; H, 3.94; N, 14.82%.

EXAMPLE 18

4-Hydroxy-3-[(2-benzyl)tetrazol-5-yl]-2-methyl-1,2-benzothiazine 1,1-Dioxide and 1-Benzyl Isomer A suspension of 4-hydroxy-2-methyl-3-(tetrazol-5-yl)-2H-1,2-benzothiazine 1,1-dioxide hemihydrate (20 g) in toluene (400 ml) was refluxed in a Dean-Stark apparatus until water removal was complete. Bis(tri-n-butyltin)oxide (35.4 ml) was then added and the reaction mixture refluxed for 30 minutes then cooled to room temperature. Benzyl bromide (8.67 ml) was then added to the clear reaction mixture which was then refluxed for 16 hours. Concentration of the mixture under reduced pressure gave a two-phase oil which was washed with n-hexane (200 ml×4) to give a dark solid (32.5 g). The solid was dissolved in trifluoroacetic acid (62 ml) and the solution cooled to 0° C. Addition of methanol (156 ml) to the solution gave a precipitate comprising an isomeric mixture of 4-hydroxy-3-[(1-benzyl)tetrazol-5-yl]-2-methyl-1,2-benzothiazine 1,1-dioxide with its 2-benzyl isomer (15.64 g). Ratio of 1-benzyl to 2-benzyl=1:0.3.

EXAMPLE 19

4-Acetoxy-3-[(2-benzyl)tetrazol-5-yl]-2-methyl-1,2-benzothiazine 1,1-Dioxide and 1-Benzyl Isomer To a solution of 4-hydroxy-2-methyl-3-(5-tetrazolyl)-2H-1,2-benzothiazine 1,1-dioxide hemihydrate (18.0 g) and potassium carbonate (4.32 g), in N,N-dimethylformamide (63 ml) was added benzylbromide (7.81 ml). After being stirred for 16 hours at room temperature, the mixture was poured into 1N HCl (500 ml) with stirring. The resulting solids were filtered off and washed with water (100 ml) and then with petroleum ether (50 ml). The wet solids were recrystallized from toluene (150 ml) to give 4-hydroxy-3-[(2-benzyl)tetrazol-5-yl]-2-methyl-1,2-benzothiazine 1,1-dioxide (16.70 g). The mother liquor contains the said compound and its 1-benzyl isomer. It was concentrated to an oil (6.03 g), which was treated with acetic anhydride (30 ml) at 110° C. for 1.5 hours, concentrated and crystallized in toluene (30 ml), to afford 4-acetoxy-3-[(2-benzyl)-tetrazol-5-yl]-2-methyl-1,2-benzothiazine 1,1-dioxide (1.31 g). The resulting mother liquor was concentrated to a viscous oil, diluted with toluene (10 ml) and seeded. The resulting crystals were filtered off and recrystallized from toluene (24 ml) to give 4-acetoxy-[(1-benzyl)tetrazol-5-yl]-2-methyl-1,2-benzothiazine 1,1-dioxide (0.602 g).

M.P.: 83°–85° C.

IR (KBr): 1780 (OCCH$_3$), 1350, 1180 cm$^{-1}$.

NMR(CDCl$_3$): 2.20 ppm (2, 3H, OAc), 2.51 (s, 3H, N—CH$_3$), 5.80 (s, 2H, CH$_2$Ar), 7.1–8.2 (m, 9H, Ar—H).

Analysis Calculated for $C_{19}H_{19}N_5O_4S$: C, 55.46; H, 4.17; N, 17.02%. Found: C, 55.08; H, 4.15; N, 16.90%.

EXAMPLE 20

4-Acetoxy-3-[(1-benzyl)tetrazol-5-yl]-2-methyl-1,2-benzothiazine 1,1-Dioxide

A mixture of the 1-benzyl isomer of Example 18 and acetic anhydride (100 ml) was refluxed for ten minutes then concentrated under reduced pressure to an oil. Addition of toluene (65 ml) to said oil afforded the title product as crystals (5.52 g; 76%; overall yield of 20% based upon the reactant of Example 18). It is identical to the product of Example 19.

EXAMPLE 21

4-Hydroxy-3-[(2-(4-methoxybenzyl))tetrazol-5-yl]-2-methyl-1,2-benzothiazine 1,1-Dioxide To a mixture of 4-hydroxy-2-methyl-3-(tetrazol-5-yl)-1,2-benzothiazine 1,1-dioxide hemihydrate (2.88 g, 10 mmole), potassium carbonate (0.69 g) and sodium iodide (0.5 g), in N,N-dimethylformamide (10 ml) was added 4-methoxybenzylchloride (1.72 g). It was stirred for four hours at room temperature then poured into water (200 ml) with stirring, and the resulting solids filtered off, washed with water and dried in vacuo to afford 3.44 g of a mixture comprising the title compound and the corresponding 1-isomer. Recrystallization from toluene give the title compound.

M.P.: 178°–181° C.

IR (KBr): 1610, 1520, 1345, 1250, 1180 cm$^{-1}$.

NMR(CDCl$_3$): 3.08 ppm (s, 3H, N—CH$_3$), 3.83 (s, 3H, OCH$_3$), 5.79 (s, 2H, —CH$_2$—Ar), 6.8–8.3 (m, Ar—H), 10.34 (s, 1H, —OH).

Analysis Calculated for $C_{18}H_{17}N_5O_4S.\frac{1}{2}$ toluene: C, 55.76; H, 4.49; N, 16.76%. Found: C, 55.92; H, 4.55; N, 17.15%.

EXAMPLE 22

3-[(2-Benzyl)tetrazol-5-yl]-2-ethyl-4-hydroxy-1,2-benzothiazine 1,1-Dioxide

A mixture of 2-ethyl-4-hydroxy-3-(tetrazol-5-yl)-1,2-benzothiazine 1,1-dioxide (0.5 g), potassium carbonate (0.120 g) and benzylbromide (0.21 ml) in dimethylformamide was stirred at room temperature for 16 hours, then poured into water (30 ml). The resulting solids were filtered off, washed with water and dried in vacuo to give crude product (0.638 g), which was recrystallized from toluene to afford the title compound (0.457 g, 70%).

M.P.: 192°–193° C.

IR (KBr): 1615, 1340, 1175 cm$^{-1}$.

NMR(CDCl$_3$): 0.82 (t, 7 Hz, 3H), 3.76 (q, 7 Hz, 2H), 5.85 (s, 2H), 7.46 (s, C$_6$H$_5$), 7.2–8.25 (m).

EXAMPLE 23

4-Acetoxy-2-methyl-3-(2-nonyl-1,3,4-oxadiazol-5-yl)-1,2-benzothiazine 1,1-dioxide A mixture of the product of Example 4 (0.50 g) and acetic anhydride (2 ml) was refluxed for about ten minutes. The reaction mixture was concentrated in vacuo. Crystallization of the residue from methanol, after filtration and drying, gave the title compound (0.493 g).

M.P.: 118°–119° C.

EXAMPLE 24

4-Cyclopentancarbonyloxy-2-ethyl-3-(2-phenyl-1,3,4-oxadiazol-5-yl)-1,2-benzothiazine 1,1-dioxide A mixture of 2-ethyl-4-hydroxy-3-(2-phenyl-1,3,4-oxadiazol-5-yl)-1,2-benzothiazine 1,1-dioxide (0.739 g), cyclopentanecarboxylic acid (0.34 g) and N,N'-dicyclohexylcarbodiimide (1.55 g) in pyridine (2.5 ml) was stirred at room temperature for 16 hours. Water (7 ml) was added to the reaction mixture and the solid thus formed was filtered and washed with water. The solid was then dissolved in chloroform and filtered. The filtrate was concentrated. The residue was recrystallized from toluene to give the title compound (0.776 g).
M.P.: 194°–196° C.

EXAMPLE 25

The following compounds were produced according to Examples indicated from appropriate corresponding reactants:

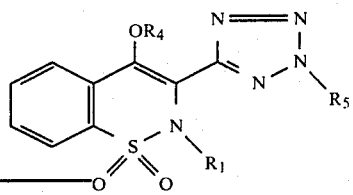

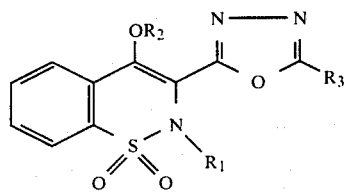

| R¹ | R² | R³ | Ex. | MP (°C.) |
|---|---|---|---|---|
| CH₃ | CH₃(CH₂)₂CO | (CH₂)₈CH₃ | 23 | 58–60 |
| CH₃ | CH₃(CH₂)₅CO | (CH₂)₈CH₃ | 23 | 53–59 |
| CH₃ | C₆H₁₁CO | (CH₂)₈CH₃ | 24 | 73–73.5 |
| CH₃ | C₆H₅CO | 4-CH₃OC₆H₄ | 5 | 178–179 |
| CH₂CH₃ | H | (CH₂)₉CH₃ | 12 | 49.5–50 |
| CH₂CH₃ | H | (CH₂)₁₀CH₃ | 12 | 60–60.5 |
| CH₂CH₃ | H | (CH₂)₁₂CH₃ | 12 | 68–69 |
| CH₂CH₃ | CH₃CO | (CH₂)₆CH₃ | 23 | 82.5–83.5 |
| CH₂CH₃ | CH₃CO | (CH₂)₈CH₃ | 23 | 75–76 |
| CH₂CH₃ | CH₃CO | (CH₂)₉CH₃ | 23 | 60.0–60.5 |
| CH₂CH₃ | CH₃CO | (CH₂)₁₀CH₃ | 23 | 57.5–58.5 |
| CH₂CH₃ | CH₃CO | (CH₂)₁₂CH₃ | 23 | 57–58 |
| CH₂CH₃ | CH₃CO | (CH₂)₁₄CH₃ | 23 | 62–63 |
| CH₂CH₃ | CH₃CO | C₆H₅ | 23 | 164.5–165 |
| CH₂CH₃ | CH₃CO | 2-CH₃C₆H₄ | 23 | 61–62 |
| CH₂CH₃ | CH₃CO | 3-CH₃C₆H₄ | 23 | 159–159.5 |
| CH₂CH₃ | CH₃CO | 4-CH₃C₆H₄ | 23 | 179–180 |
| CH₂CH₃ | CH₃CO | 4-(CH₃(CH₂)₃O)—C₆H₄ | 23 | 155.5–156.5 |
| CH₂CH₃ | CH₃CO | 3,4-di-(CH₃O)—C₆H₃ | 23 | 188–189 |
| CH₂CH₃ | CH₃(CH₂)₂CO | C₆H₅ | 23 | 156–157 |
| CH₂CH₃ | (CH₃)₂CHCO | C₆H₅ | 23 | 170–171 |
| CH₂CH₃ | CH₃(CH₂)₄CO | C₆H₅ | 23 | 119–120 |
| CH₂CH₃ | CH₃(CH₂)₆CO | C₆H₅ | 23 | 83–84 |
| CH₂CH₃ | CH₃(CH₂)₂CHCO<br>\|<br>CH₃ | C₆H₅ | 23 | 148–149 |
| CH₂CH₃ | C₃H₅CO | C₆H₅ | 24 | 158–159 |
| CH₂CH₃ | C₄H₇CO | C₆H₅ | 24 | 173–174 |
| CH₂CH₃ | C₅H₉CO | C₆H₅ | 24 | 181–183 |
| CH₂CH₃ | C₆H₁₁CO | C₆H₅ | 24 | 194–196 |
| CH₂CH₃ | 4-(CH₃O)—C₆H₄CO | C₆H₅ | 5 | 190–193 |
| CH₂CH₃ | 4-(NO₂)—C₆H₄CO | C₆H₅ | 5 | 264 (dec) |
| CH₂CH₂CH₃ | H | (CH₂)₈CH₃ | 12 | 53–53.5 |
| CH₂CH₂CH₃ | CH₃CO | (CH₂)₈CH₃ | 23 | 160 |
| CH₂CH₂CH₃ | C₆H₅CO | C₆H₅ | 5 | 173–175 |
| CH(CH₃)₂ | H | (CH₂)₈CH₃ | 12 | 73–74.5 |
| CH(CH₃)₂ | C₆H₅CO | C₆H₅ | 5 | 169.5–171 |

EXAMPLE 26

The compounds listed below were prepared according to Examples indicated from appropriate corresponding reactants:

| R¹ | R⁴ | R⁵ | Ex. | MP (°C.) |
|---|---|---|---|---|
| CH₃ | H | CH₃ | 16(a) | 228–232 |
| CH₃ | H | CH₂CH=CH₂ | 16(a) | 156–159 |
| CH₃ | H | CH₂C(CH₃)=CH₂ | 16(a) | 164–166 |
| CH₃ | H | CH₂CH=CHC₆H₅ | 16(a) | 192–194 |
| CH₃ | H | CH₂CH₂C₆H₅ | 16(a) | 172–175 |
| CH₃ | H | CH₂(CH₂)₂C₆H₅ | 16(a) | 159.5–162 |
| CH₃ | H | 4-(NO₂)C₆H₄ | 16(a) | 212–214 |
| CH₃ | ClCH₂CO | ClCH₂CO | 16 | 120 (dec) |
| CH₃ | CH₃CO | CH₂(4-(CH₃O)C₆H₄) | 16 | 175 |
| CH₂CH₃ | H | CH₂C₆H₅ | 16(a) | 192–193 |
| CH₂CH₃ | CH₃CO | (CH₂)₇CH₃ | 16 | 81.5–82 |
| CH₂CH₃ | CH₃CO | (CH₂)₈CH₃ | 16 | 69.5 |
| CH₂CH₃ | CH₃CO | (CH₂)₉CH₃ | 16 | 68.5–69 |
| CH₂CH₃ | CH₃CO | (CH₂)₁₀CH₃ | 16 | 72 |
| CH₂CH₃ | CH₃CO | (CH₂)₁₁CH₃ | 16 | 72.5 |

-continued

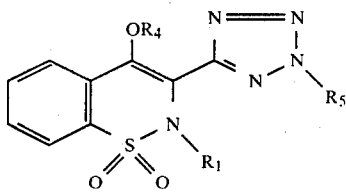

| R¹ | R⁴ | R⁵ | Ex. | MP (°C.) |
|---|---|---|---|---|
| CH₂CH₃ | CH₃CO | (CH₂)₁₃CH₃ | 16 | 68 |
| CH₂CH₃ | CH₃CO | CH₂(2-CH₃C₆H₄) | 16 | 186–187 |
| CH₂CH₃ | CH₃CO | CH₂(3-CH₃C₆H₄) | 16 | 168.5 |
| CH₂CH₃ | CH₃CO | CH₂(4-(CH₃)C₆H₄) | 16 | 157–158 |
| CH₂CH₃ | C₆H₅CO | CH₂(2-CH₃C₆H₄) | 17 | 168–169 |
| CH₂CH₃ | C₆H₅CO | CH₂(3-CH₃C₆H₄) | 17 | 122–125 |
| CH₂CH₃ | C₆H₅CO | CH₂(4-CH₃C₆H₄) | 17 | 135.5–136 |
| CH₂CH₂CH₃ | CH₃CO | CH₂(4-(CH₃O)C₆H₄) | 16 | 115–116 |

EXAMPLE 27

A dry solid pharmaceutical composition is prepared by blending the following materials together in the proportions by weight specified below:

| | |
|---|---|
| 4-Hydroxy-2-methyl-3-(2-nonyl-1,3,4-oxadiazol-5-yl)-1,2-benzothiazine 1,1-dioxide | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 100 mg of the active ingredient. Other tablets are also prepared in a similar manner containing 5, 10, 25 and 50 mg of the active ingredient, respectively, by merely using the appropriate amount of the appropriate 5-LO inhibitor compound in each case.

EXAMPLE 28

A dry solid pharmaceutical composition is prepared by combining the following materials together in the proportions by weight indicated below:

| | |
|---|---|
| 4-Benzoyloxy-2-ethyl-3-(2-phenyl-1,3,4-oxadiazol-5-yl)-1,2-benzothiazine 1,1-dioxide | 50 |
| Calcium carbonate | 20 |
| Polyethylene glycol, average molecular weight 4000 | 30 |

The dried solid mixture so prepared is then thoroughly agitated so as to obtain a powdered product that is completely uniform. Soft elastic and hard-filled gelatin capsules containing this pharmaceutical composition are then prepared, employing a sufficient quantity of material in each case so as to provide each capsule with 250 mg of the active ingredient.

EXAMPLE 29

Oral Suspension

One thousand ml of an aqueous suspension, containing 100 mg of 4-benzoyloxy-2-(2-methoxyethoxymethyl)-3-(2-phenyl-1,3,4-oxadiazol-5-yl)-1,2-benzothiazine 1,1-dioxide in each 5 ml dose, is prepared using the following ingredients:

| | |
|---|---|
| Benzothiazine 1,1-dioxide compound | 20 g |
| Citric acid | 2 g |
| Benzoic acid | 1 g |
| Sucrose | 700 g |
| Tragacanth | 5 g |
| Lemon oil | 2 g |
| Deionized water, q.s. | 1000 ml |

All ingredients except the benzothiazine 1,1-dioxide compound are thoroughly dispersed in sufficient water to make 850 ml of suspension. The benzothiazine 1,1-dioxide compound is then stirred in until uniformly distributed and sufficient water added to make 1000 ml.

PREPARATION 1 o-Carbomethoxy-N-cyanomethylbenzenesulfonamide

To a suspension of N-cyanomethylsaccharin (276 g) in methanol (1000 ml) was added dropwise 28% sodium methoxide (145 ml) over 30 minutes at 5°–10° C. After stirring at 5°–10° C. for 1 hour, 6N HCl (ca. 230 ml) was added dropwise maintaining the temperature at 10°–15° C. The resulting crystals were collected by filtration, washed with water and dried in vacuo at 50° C. for 16 hours to give o-carbomethoxy-N-cyanomethylbenzenesulfonamide, 264 g (78.7%).

M.P.: 110° C.

IR (CHCl₃): 1720, 1170 cm⁻¹.

NMR(CDCl₃): 4.05 (s, 3H), 4.10 (d, J=7 Hz, 2H), 6.90 (t, J=7 Hz, 1H), 7.6–8.4 (m).

PREPARATION 2 o-Carbomethoxy-N-cyanomethyl-N-methylbenzenesulfonamide

To a mixture of o-carbomethoxy-N-cyanomethylbenzenesulfonamide (116 g) and sodium hydroxide (16.8 g) in water (80 ml) and acetone (400 ml) was added methyliodide (28 ml) at 20°–25° C. After stirring for 3 hours at 20° C., the solvent was stripped off to give a viscous oil. Water (400 ml) was added and the mixture extracted with dichloromethane. The resulting extract was washed with water, dried over sodium sulfate and concentrated to give the product as a viscous oil, 108.2 g (88%).

IR (CHCl₃): 1730, 1355, 1290, 1165 cm⁻¹

NMR(CDCl₃): 83.02 (s, 3H, N—CH₃), 4.00 (s, 3H, OCH₃), 4.34 (s, 2H, —CH₂—CN), 7.5–8.2 (m, 4H).

PREPARATION 3

3-Cyano-4-hydroxy-2-methyl-1,2-benzothiazine 1,1-Dioxide

To a solution of o-carbomethoxy-N-cyanomethyl-N-methylbenzenesulfonamide (108 g) in toluene (600 ml) was added 28% sodium methoxide-methanol solution (83 ml) with vigorous stirring. After 2 hours the solvent was evaporated to ca. 400 ml and water (800 ml) added to dissolve the viscous residue. The pH was adjusted to ca. 2 with 6N HCl. The resulting crystals were granulated for 1 hour, filtered off, washed with water and dried in vacuo to give the title product, 77.2 g (81.1%). Purified product was obtained in 75% yield by dissolving the compound (3.3 g) in isopropanol, followed by dropwise addition of water (35 ml).

M.P.: 157.0°–158.0° C.

IR (KBr): 2220, (CN), 1350, 1180 (SO₂) cm⁻¹.

NMR(CDCl₃): 3.23 (s, 3H, N—CH₃), 7.6–8.4 (m, 4H)
Mass (EI): m/e 235 (M), 172 (M—SO₂).
Analysis Calculated for C₁₀H₈N₂O₃S: C, 50.84; H, 3.41; N, 11.86%. Found: C, 50.84; H, 3.48; N, 11.69%.

PREPARATION 4

3-Cyano-2-ethyl-4-hydroxy-1,2-benzothiazine 1,1-Dioxide

A mixture of o-carbomethoxy-N-cyanomethylbenzenesulfonamide (6.25 g) (0.025 moles), ethyl iodide (2 ml) and potassium carbonate (1.73 g) in dimethylformamide (30 ml) was stirred at room temperature for 48 hours at at 50° C. for 2 hours. The resulting mixture was poured into water (50 ml) and extracted with dichloromethane. The extract was washed with water, dried over sodium sulfate and concentrated to give an oil, 6.69 g. The oil was dissolved in toluene (33 ml), then 28% sodium methoxide in methanol (4.6 ml) was added. After being stirred at 20° C. for 16 hours, the mixture was concentrated to a viscous oil, to which was added water (50 ml) and then 6N HCl to pH 2.0. The resulting solid was filtered off, washed with water and dried in vacuo to give colorless crystals (4.83 g). Recrystallization from dichloroethane afforded colorless needles of desired product, 4.215 g (67.4%).
M.P.: 157° C.
IR (KBr): 2310, 1360, 1180 cm⁻¹.
NMR (acetone, D₆): 0.96 (t, J=7 Hz, 3H), 3.65 (q, J=7, 2H), 7.8–8.2 (m, 4H).

In like manner, but using n-propyl iodide or isopropyl iodide in place of ethyl iodide, the corresponding 2-n-propyl- and 2-isopropyl compounds are prepared:

3-cyano-2-n-propyl-4-hydroxy-1,2-benzothiazine 1,1-dioxide
M.P.: an oil
IR (CHCl₃): 2310, 1360, 1180 cm⁻¹.
NMR (CDCl₃): 0.77 (t, J=7 Hz, 3H), 1.48 (hex, J=7 Hz, 2H), 3.57 (t, J=7 Hz, 2H), 7.5–8.2 (m, 4H).

3-cyano-2-isopropyl-4-hydroxy-1,2-benzothiazine 1,1-dioxide
M.P.: 149°–153° C.
IR (KBr): 2240, 1350, 1185 cm⁻¹.
NMR (CDCl₃): 1.16 (d, J=7 Hz, 6H), 4.37 (pent, J=7 Hz, 1H), 7.5–8.3 (m, 4H).

PREPARATION 5

3-Cyano-4-hydroxy-2-(2-methoxyethoxymethyl)-1,2-benzothiazine 1,1-Dioxide

To a solution of o-carbomethoxy-N-cyanomethyl-benzenesulfonamide (6.25 g) in dichloromethane (50 ml) was added triethylamine (2.5 g) and then beta-methoxyethoxymethyl chloride (3.12 g) at 5°–10° C. After being stirred for 1 hour at room temperature, the mixture was washed with water, dried over sodium sulfate and concentrated. To the resulting oil was added toluene (33 ml) and then 28% sodium methoxide in methanol (4.6 ml) and stirring was continued for an additional 16 hours at room temperature. The mixture was extracted with water (50 ml) and the aqueous layer was acidified to pH 2 with 6N HCl and extracted with dichloromethane. The resulting organic layer was washed with water, dried over sodium sulfate and concentrated to a viscous oil, which was submitted to silica gel column chromatography (SiO₂, 100 g) and eluted with a mixed solvent (CH₂Cl₂:CH₃OH 4:1) to give the title product as a viscous oil.
IR (CHCl₃): 2220, 1360, 1185 cm⁻¹.

NMR (CDCl₃): 3.23 (s, 3H), 3.1–3.7 (m, 4H), 5.1 (s, 3H), 7.5–8.2 (m).

We claim:

1. A compound having the formula

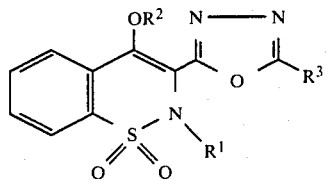

wherein
R¹ is alkyl having from 1 to 8 carbon atoms or —(CH₂)ₘ—O—(CH₂)ₙOR⁶ where m and n are each an integer from 1 to 4 and R⁶ is alkyl having from one to six carbon atoms;
R² is hydrogen, alkanoyl having from 2 to 15 carbon atoms, cycloalkylcarbonyl having from 3 to 8 carbon atoms in the cycloalkyl moiety, benzoyl or benzoyl ring substituted with F, Cl, Br, I, CF₃, CH₃, NO₂ or CH₃O; and
R³ is alkyl having from 1 to 15 carbon atoms, thienyl, furyl, cycloalkyl having from 3 to 8 carbon atoms, phenyl or phenyl substituted with F, Cl, Br, I, CF₃, CH₃ or CH₃O.

2. A compound according to claim 1 wherein R² is hydrogen, alkanoyl having from 2 to 10 carbon atoms, benzoyl or cyclohexylcarbonyl, and R³ is alkyl having from 7 to 15 carbon atoms, phenyl or tolyl.

3. A compound according to claim 2 wherein R¹ is alkyl having from 1 to 3 carbon atoms.

4. A compound according to claim 3 wherein R² is hydrogen, benzoyl, acetyl or cyclohexylcarbonyl.

5. The compound according to claim 4 wherein R¹ is ethyl, R² is acetyl and R³ is m-tolyl.

6. The compound according to claim 4 wherein R¹ is ethyl, R² is acetyl and R³ is phenyl.

7. The compound according to claim 4 wherein R¹ is ethyl, R² is cyclohexylcarbonyl and R³ is phenyl.

8. The compound according to claim 4 wherein R¹ is methyl, R² is cyclohexylcarbonyl and R³ is nonyl.

9. The compound according to claim 4 wherein R¹ is ethyl, R² is benzoyl and R³ is phenyl.

10. A compound having the formula

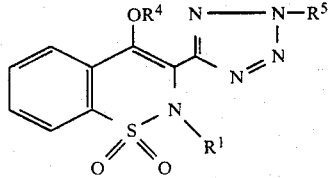

where
R¹ is alkyl having from 1 to 8 carbon atoms or —(CH₂)ₘ—O—(CH₂)ₙ—OR₆ where m and n are each an integer from 1 to 4 and R⁶ is alkyl having from one to six carbon atoms;
R⁴ is hydrogen, alkanoyl having from 2 to 15 carbon atoms, benzoyl or benzoyl ring substituted with F, Cl, Br, I, CF₃, CH₃, CH₃O; and
R⁵ is hydrogen, alkyl having from 1 to 15 carbon atoms, alkanoyl having from 2 to 15 carbon atoms, alkenyl, aralkenyl cycloakyl of from 3 to 8 carbon atoms, phenylethyl, cycloalkylcarbonyl having from 3 to 8 carbon atoms in the cycloalkyl moiety, benzoyl, benzoyl substituted with F, Cl, Br, I, $CF_3$, $CH_3$, $CH_3O$ or $NO_2$, furylmethyl, thienylmethyl, benzyl or benzyl ring substituted with F, Cl, Br, I, $CF_3$, $CH_3$, $NO_2$ or $CH_3O$.

11. A compound according to claim 10 wherein $R^1$ is alkyl having from 1 to 3 carbon atoms, $R^4$ is acetyl and $R^5$ is alkyl having from 8 to 10 carbon atoms, methylbenzyl or methoxybenzyl.

12. The compound according to claim 11 wherein $R^1$ is ethyl, $R^4$ is acetyl and $R^5$ is nonyl.

13. The compound according to claim 11 wherein $R^1$ is n-propyl, $R^4$ is acetyl and $R^5$ is 4-methoxybenzyl.

14. The compound according to claim 11 wherein $R^1$ is ethyl, $R^4$ is acetyl and $R^5$ is 3-methylbenzyl.

15. A compound according to claim 10 wherein $R^1$ is alkyl having from 1 to 3 carbon atoms, and each of $R^4$ and $R^5$ is hydrogen.

16. The compound according to claim 15 wherein $R^1$ is methyl.

17. The compound according to claim 15 wherein $R^1$ is ethyl.

18. The compound according to claim 15 wherein $R^1$ is n-propyl.

* * * * *